United States Patent
Roy et al.

(10) Patent No.: US 10,889,547 B2
(45) Date of Patent: Jan. 12, 2021

(54) METHOD FOR THE PURIFICATION OF ETHOXYQUIN

(71) Applicant: BASF SE, Ludwigshafen am Rhein (DE)

(72) Inventors: Sumana Roy, Lampertheim (DE); Andreas Keller, Ludwigshafen am Rhein (DE); Wolfgang Siegel, Ludwigshafen am Rhein (DE); Michael Joedecke, Ludwigshafen am Rhein (DE); Martin Haubner, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/311,206

(22) PCT Filed: Jun. 22, 2017

(86) PCT No.: PCT/EP2017/065414
§ 371 (c)(1),
(2) Date: Dec. 19, 2018

(87) PCT Pub. No.: WO2018/001862
PCT Pub. Date: Jan. 4, 2018

(65) Prior Publication Data
US 2019/0233378 A1    Aug. 1, 2019

(30) Foreign Application Priority Data

Jun. 29, 2016 (EP) .................................. 16176852
Sep. 28, 2016 (EP) .................................. 16191008

(51) Int. Cl.
*C07D 215/20* (2006.01)
*B01D 3/14* (2006.01)
(Continued)

(52) U.S. Cl.
CPC .......... *C07D 215/20* (2013.01); *A23K 20/132* (2016.05); *A23L 3/3526* (2013.01);
(Continued)

(58) Field of Classification Search
CPC . B01D 3/10; B01D 3/14; B01D 3/141; B01D 3/143; C07D 215/20; B01J 19/305; A23L 3/3526; A23K 20/132
See application file for complete search history.

(56) References Cited

U.S. PATENT DOCUMENTS 2,471,134 A    5/1949   Wright
4,230,533 A    10/1980  Giroux
(Continued)

FOREIGN PATENT DOCUMENTS

CA    1222717 A    6/1987
CA    1242309 A    9/1988
(Continued)

OTHER PUBLICATIONS

Wolff, E.A. et al. (1995) Industrial and Engineering Chemistry Research, 34, 2094-2103.*
(Continued)

*Primary Examiner* — Brian A McCaig
(74) *Attorney, Agent, or Firm* — Faegre Drinker Biddle & Reath LLP

(57) ABSTRACT

The present invention relates to a process for purifying ethoxyquin by distillation, to high-purity ethoxyquin obtainable by means of distillative purification and to the use thereof, particularly as additive in foodstuffs and feedstuffs.

11 Claims, 3 Drawing Sheets

Structure of ethoxyquin

(51) Int. Cl.
  *A23K 20/132* (2016.01)
  *A23L 3/3526* (2006.01)
  *B01D 3/10* (2006.01)
  *B01J 19/30* (2006.01)

(52) U.S. Cl.
  CPC ............... *B01D 3/10* (2013.01); *B01D 3/14* (2013.01); *B01D 3/141* (2013.01); *B01D 3/143* (2013.01); *B01J 19/305* (2013.01); *A23V 2002/00* (2013.01); *A23V 2200/02* (2013.01)

(56) References Cited

U.S. PATENT DOCUMENTS

| | | | |
|---|---|---|---|
| 4,772,710 A * | 9/1988 | von Magius | A01N 43/42 |
| | | | 546/178 |
| 5,785,819 A | 7/1998 | Kaibel et al. | |
| 8,674,140 B2 | 3/2014 | Schmidt et al. | |
| 2011/0200705 A1* | 8/2011 | Tricarico | A23K 10/16 |
| | | | 426/2 |
| 2016/0176803 A1 | 6/2016 | Weingarten et al. | |
| 2016/0194272 A1 | 7/2016 | Weingarten et al. | |
| 2016/0194273 A1 | 7/2016 | Weingarten et al. | |

FOREIGN PATENT DOCUMENTS

| | | |
|---|---|---|
| DE | 3522234 C2 | 2/1994 |
| EP | 122367 A2 | 10/1984 |
| EP | 126288 A2 | 11/1984 |
| EP | 133510 A1 | 2/1985 |
| EP | 640367 A1 | 3/1995 |
| EP | 780147 A2 | 6/1997 |
| JP | S4935387 A | 4/1974 |
| WO | WO-2010031790 A1 | 3/2010 |

OTHER PUBLICATIONS

European Search Report for EP Patent Application No. 16191008.8, dated Jan. 17, 2017, 3 pages.
Gerd Kaibel, "Distillation Columns with Vertical Partitions", Chemical Engineering and Technology, vol. 10, Issue 1, 1987, pp. 92-98.
He, et al., "Purification of Ethoxyquin and Its Two Oxidation Products", Journal of Agricultural and Food Chemistry, vol. 48, Issue 8, 2000, pp. 3069-3071.
Chai, X., et al., "Determination of the Solubility of a Monomer in Water by Multiple Headspace Extraction Gas Chromatography", Journal of Applied Polymer Science, 2006, vol. 99, pp. 1296-1301.
Kaibel, et al., "Gestaltung destillativer Trennungen Linter Einbeziehung thermodynamischer Gesichtspunkte", Chemie Ingenieur Tecnik, vol. 61, Issue 1, Jan. 30, 1989, pp. 16-25.
Kaibel, et al., "Thermodynamics—guideline for the development of distillation column arrangements", Gas Separation and Purification, vol. 4, Issue 2, Jun. 1990, pp. 109-114.
Lestak, et al., "Advanced Distillation saves Energy and Capital", Chemical Engineering, Issue 7, Jul. 1997, pp. 72-76.
Wolff, et al., "Operation of Integrated Three-Product (Petlyuk) Distillation Columns", Industrial & Engineering Chemistry Research, vol. 34, Issue 6, 1995, pp. 2094-2103.
International Search Report for PCT/EP2017/065414 dated Jul. 17, 2017.
Written Opinion of the International Searching Authority for PCT/EP2017/065414 dated Jul. 17, 2017.

* cited by examiner

FIG 1: Structure of ethoxyquin (Figure 1)
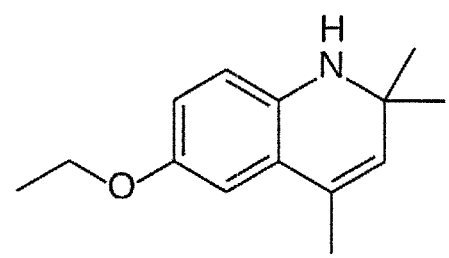

FIG 2: Dividing wall column used according to the invention (Figure 2)
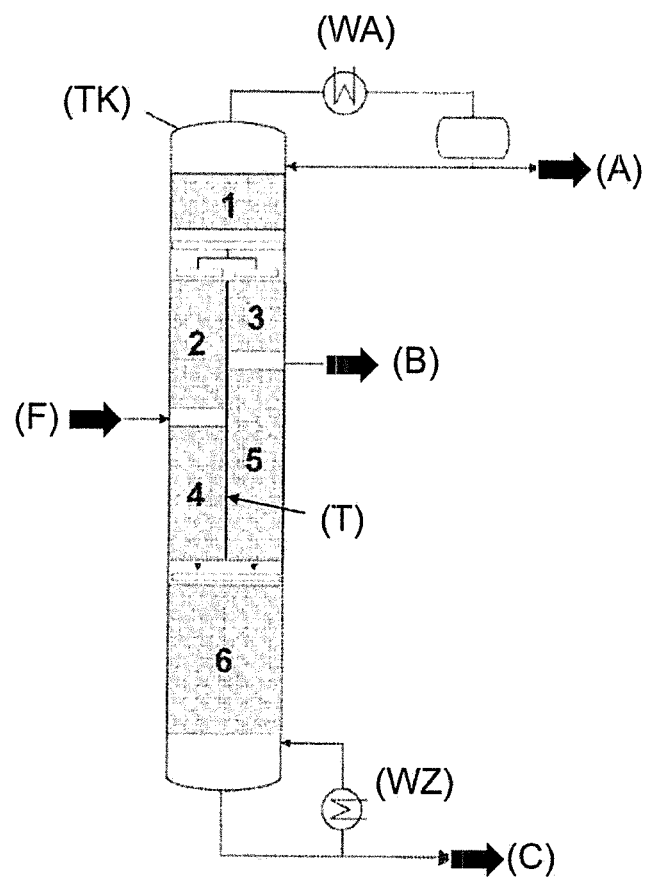

FIG 3: Dividing wall column used according to the invention – diagram (Figure 3)
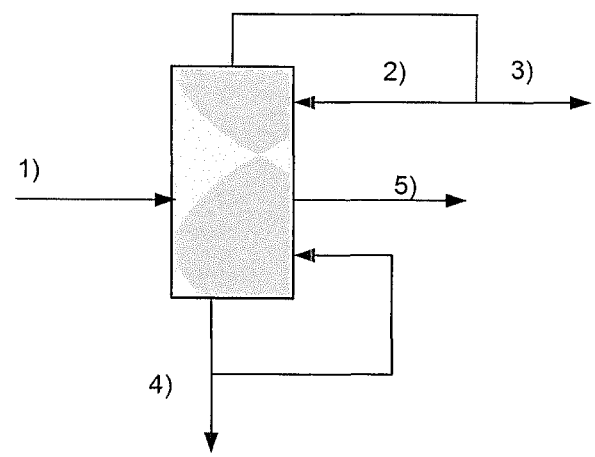

METHOD FOR THE PURIFICATION OF ETHOXYQUIN

CROSS-REFERENCE TO RELATED APPLICATIONS

This application is a national stage application (under 35 U.S.C. § 371) of PCT/EP2017/065414, filed Jun. 22, 2017, which claims benefit of European Application Nos. 16176852.8, filed Jun. 29, 2016, and 16191008.8, filed Sept. 28, 2016, all of which are incorporated herein by reference in their entirety.

The present invention relates to a process for purifying ethoxyquin by distillation, to high-purity ethoxyquin obtainable by means of distillative purification and to the use thereof, particularly as additive in foodstuffs and feedstuffs.

Ethoxyquin as such is known, likewise purification thereof by means of various basic technical operations. However, it has not been possible to date to obtain high-purity ethoxyquin and particularly not ethoxyquin of a kind comprising less than 100 ppm, preferably less than 50 ppm, particularly preferably less than 10 ppm and especially preferably less than 5 ppm such as, for example less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

Since p-phenetidine is known as a substance of toxicological concern however, depletion thereof in ethoxyquin as far as possible is urgently desired. Until now, purification processes have not managed to provide ethoxquin having a p-phenetidine content of less than 0.1 percent (corresponding to 1000 ppm).

Ethoxyquin (FIG. 1) is the trivial name of 1,2-dihydro-6-ethoxy-2,2,4-trimethylquinoline and has the CAS number 91-53-2 and the E number 324.

Owing to its known antioxidant effect, ethoxyquin has been used for decades largely for feedstuff preservation, since it inhibits or at least delays, inter alia, the oxidation of fats and vitamins.

Ethoxyquin may be obtained, for example, starting from p-chloronitrobenzene and sodium methoxide, hydrogenation of the resulting reaction product to give p-phenetidine and subsequent reaction with acetone to give ethoxyquin (see for example Thomas A. Unger: Pesticide Synthesis Handbook. William Andrew, 1996, p. 586)

p-Phenetidine is present as known impurity in ethoxyquin if it has been prepared by the synthetic route via p-phenetidine. It was therefore an aim to deplete this secondary component in the ethoxyquin product.

P-Phenetidine has a melting point of 3° C. and a boiling point of 254° C. Ethoxyquin has a melting point of below zero ° C. and a boiling point of about 123 to 125° C. at 2.67 hPa.

Customary methods for separating two organic substances are described, for example, in "Separation Processes, Introduction", C. Judson King, in Ullmann's Encyclopedia of Industrial Chemistry, 2012. It is evident from this that a person skilled in the art presented with the object of purifying ethoxyquin would not have used distillation as industrial scale process. On the contrary, the person skilled in the art is informed therein that, in the case of a problem of separating minor impurities from an organic product (i.e. a fine purification), particularly adsorptive processes, precipitations/washing with acid, chromatographic methods, stripping or crystallization should be the most promising basic operations. According to Ullmann in contrast, distillation is used for coarse purification, i.e. depletion of a component before the product stream is then fed to a fine purification as noted above.

According to Ullmann in contrast, in the case of such a problem in fine purification of ethoxyquin, distillation is not an advisable best process step.

Ping He and Robert G. Ackmann, Journal of Agricultural and Food Chemistry, Volume 48, Number 8, August 2000, pages 3069 to 3071, "Purification of Ethoxyquin and its two Oxidation Products", describe various purification methods of ethoxyquin and the ethoxyquin dimer and a further substance. In this case, ethoxyquin was enriched by distillation under reduced pressure to a purity of about 90 percent (area percent) and then concentrated by column chromatography to a purity of greater than 99 percent. Purification of ethoxyquin having less than 500 ppm p-phenetidine is not disclosed, neither by distillation nor by other methods.

No patent literature is known which discloses the provision of ethoxyquin having a purity of less than 1000 ppm p-phenetidine.

So far unknown, therefore, is a method for providing ethoxyquin at very high purity having less than 100 ppm p-phenetidine, especially no industrial scale process. In particular, no commercial industrial product is known which would meet these requirements.

Therefore, the object of the present invention is to provide ethoxyquin, the p-phenetidine content of which should be less than 100 ppm and in particular as low as possible in order to take into consideration all toxicological concerns in the use of ethoxyquin with respect to its p-phenetidine impurity.

BRIEF DESCRIPTION OF THE DRAWINGS

FIG. 1 shows the structure of ethoxyquin.

FIG. 2 shows an exemplary dividing wall column used as described herein.

FIG. 3 shows a diagram of a dividing wall column used as described herein.

DETAILED DESCRIPTION OF THE INVENTION

A process for purifying ethoxyquin comprising p-phenetidine has been found comprising at least one step of distillation, preferably comprising no further purification steps such as adsorption, washing, crystallization, particularly preferably comprising only one or more distillation steps, especially preferably comprising only one or two distillation steps, wherein ethoxyquin may be obtained comprising less than 100 ppm, preferably less than 50 ppm, particularly preferably less than 10 ppm and especially preferably less than 5 ppm such as, for example, less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

Furthermore, it has been found that ethoxyquin is obtainable by the process according to the invention comprising less than 100 ppm, preferably less than 50 ppm, particularly preferably less than 10 ppm and especially preferably less than 5 ppm such as, for example less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

Furthermore, ethoxyquin has been found comprising less than 100 ppm, preferably less than 50 ppm, particularly preferably less than 10 ppm and especially preferably less than 5 ppm, such as, for example less than 1 ppm or even less than 0.5 ppm p-phenetidine and also all values inbetween, for example, less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

Furthermore, the use of ethoxyquin, obtainable for example by the process according to the invention, comprising less than 100 ppm, preferably less than 50 ppm, particularly preferably less than 10 ppm and especially preferably less than 5 ppm such as for example, less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1, has been found as additive in foodstuffs and feedstuffs, preferably in feedstuffs, wherein ethoxyquin is used as antioxidant, particularly preferably as antioxidant in feedstuffs and feed additives.

The method can be carried out as elucidated below at various scales depending on the desired amount of ethoxyquin. The basic principle and the basic setup of the apparatus is comparable here in both cases: adaptations are especially a result of the dimensions of the plant. A possible necessary adjustment to the actual dimensions and configuration of the apparatuses is easily possible to a person skilled in the art in the context of the requirements elucidated below.

The distillation according to the invention can be carried out batchwise or continuously. The continuous mode is preferred. In particular; relatively large amounts of ethoxyquin according to the invention can be provided by means of continuous distillation.

In the context of operating a process for providing a product according to the present invention, it has been recognized that, in the case of skilful performance of the distillation using a so-called dividing wall column, even a one-stage distillation step is sufficient to obtain ethoxyquin comprising less than 100 ppm phenetidine. By appropriate adjustment of the parameters and optionally a further distillation step, ethoxyquin products can thus be obtained even comprising extremely low fractions of p-phentidine down to virtually no p-phenetidine.

A suitable dividing wall column of this kind is known to those skilled in the art, for example from U.S. Pat. Nos. 2,471,134, 4,230,533, EP122367A, EP 126288A, EP133510A, WO2010/031790, and from Chem. Eng. Technol, 10, 1987, pages 92 to 98, Chem. Ing. Tech. 61, 1989, No. 1, pages 16-25, Gas Separation and Purification 4, 1990, pages 109 to 114, Process Engineering 2, 1993, pages 33 and 34, Trans IChemE 72, 1994, Part A, pages 639 to 644, Chemical Engineering 7, 1997, pages 72 to 76.

In this construction type, a dividing wall is mounted in the middle region above and below the feed point and the side draw which seals the inflow section 2, 4 in relation to the offtake section 3, 5 and in this column section prevents transverse mixing of liquid and vapor streams. This reduces the total number of distillation columns required in the fractionation of multicomponent mixtures. As in conventional side takeoff columns, intermediate vaporizers and intermediate condensers can also be used in dividing wall columns. Intermediate condensers are preferably mounted at the upper end of the dividing wall or in the common column region 1 above the dividing wall. Intermediate vaporizers are preferably mounted at the lower end of the dividing wall or in the common column region 6 below the dividing wall.

A dividing wall column can also be replaced by the arrangement of thermally coupled distillation columns with the same energy consumption. A description of thermally coupled distillation columns, which can be constructed in varying apparatus configuration, is also found in the technical literature in the places mentioned above. It is also possible to equip the individual subcolumns completely with evaporators and condensers. This corresponds to a dividing wall column having an intermediate vaporizer and intermediate condenser. A particular advantage of this specific configuration is that the individual columns can also be operated at different pressures. This enables too high temperature differences to be avoided and operating temperatures to be adjusted better to predefined heating and cooling media. The possibilities for energy network measures are improved.

A further design of dividing wall columns that can be used in accordance with the invention is provided where the dividing wall may be extended in a continuous manner either to the upper or to the lower end of the distillation column (FIG. 2). This design corresponds to the arrangement of a main column with associated side column. In the case of this embodiment, no energy cost advantages, but investment cost advantages, are to be expected compared to conventional column arrangements.

Dividing wall columns and thermally coupled distillation columns offer advantages both in terms of energy demand and investment costs compared to the arrangement of conventional distillation columns. To control dividing wall columns and thermally coupled columns, various control strategies are described. Descriptions are found in: U.S. Pat. No. 4,230,533, DE 35 22 234 C2, EP 780 147 A, Process Engineering 2 (1993), 33-34, and Ind. Eng. Chem. Res. 34 (1995), 2094 2103.

A typical dividing wall column (TK) to be used in the process according to the invention (see FIG. 2 of WO2010/031790) in each case has a dividing wall (T) in the longitudinal direction of the column forming an upper common column region (1), a lower common column region (6), an inflow section (2, 4) with rectifying section (2) and stripping section (4), and an offtake section (3, 5) with rectifying section (5) and stripping section (3), wherein the mixture to be separated (feed) is fed to the middle region of the inflow section (2, 4), the high boiler fraction is removed via the bottom (bottom takeoff C), the low boiler fraction is removed via the overhead (top takeoff A) and the intermediate boiler fraction is removed from the middle region of the offtake section (3, 5) (side takeoff B).

The dividing wall column(s) of the process according to the invention each has/have preferably 30 to 100, especially 50 to 90, theoretical plates.

A typical dividing wall column in the context of the present invention each has preferably a dividing wall (T) in the longitudinal direction of the column forming an upper (C) and lower (D) common column region, an inflow section (A) and offtake section (B). The mixture to be separated is fed to the middle part of the inflow region and the product EQ is removed from the middle region of the offtake section.

In particular, in the process according to the invention, the upper common column region (1) of the dividing wall column(s) (TK) has 5 to 50%, preferably 20 to 35%, the rectifying section (2) of the inflow section (2, 4) of the column has 5 to 50%, preferably 10 to 20%, the stripping section (4) of the inflow section of the column has 5 to 50%, preferably 20 to 35%, the rectifying section (3) of the offtake section (3, 5) of the column has 5 to 50%, preferably 7 to 20%, the stripping section (5) of the offtake section of the column has 5 to 50%, preferably 20 to 35%, and the common lower region (6) of the column has 5 to 50%, preferably 20 to 35%, of the total number of theoretical plates (nth) of the column. The sum total here adds up to 100 (one hundred) percent.

In particular, in the dividing wall column(s) (TK), in each case the sum of the number of theoretical plates of the subregions (2) and (4) in the inflow section is 80 to 110%, preferably 90 to 100%, of the total of the number of plates of the subsections (3) and (5) in the offtake section. The sum total here adds up to 100 (one hundred) percent.

The dividing wall section preferably has 40-80%, preferably 50-70%, the upper common column section has 5-50%, preferably about 15-20%, the lower common column section has 5-50%, preferably about 15-20%, of the total number of theoretical plates of the column. The sum total here adds up to 100 (one hundred) percent.

The dividing wall column consists of a column (as described above) with a heat exchanger as vaporizer and a heat exchanger as condenser (see FIG. 3).

The column flows are (see FIG. 3): 1) feed stream to the column, 3) distillate defined as a defined portion of the condensed vapor stream, the 5) side takeoff, and 4) the bottom takeoff defined as a defined portion of the bottom stream. The reflux 2) of the column defined as a defined portion of the condensed vapor stream which is recirculated to the upper common section of the column (C). The bottom stream was evaporated by means of a vaporizer at 190-220° C. and fed to the lower common section of the column (D). Vaporizers as such, advantages and disadvantages of different vaporizer types and also application thereof are well known to those skilled in the art, for example from Lexicon Römpp (Thieme-Verlag), keyword "Dünnschichtverdampfer" [thin-film evaporator] (for example the update of August 2004); briefly presented therein are, for example, falling-film evaporators/falling-stream evaporators, rotary thin-film evaporators, centrifugal thin-film evaporators. Further relevant fundamental technical literature is also Vauck and Müller "Grundoperationen chemischer Verfahrenstechnik [Basic operations of chemical process technology], 11th edition, 2000, Deutscher Verlag für Grundstoffindustrie; Sattler "Thermische Trennverfahren" [Thermal Separation Processes], 2nd edition, 2001, Wiley-VCH; Gnielinski, Mersmann, Thurner, "Verdampfung, Kristallisation, Trocknung" [Evaporation, Crystallization, Drying], Vieweg-Verlag 1993.

If particularly high requirements of the purities of the ethoxyquin products are demanded, it is favorable and especially preferred in the context of this invention to equip the dividing wall with thermal insulation. A description of the various possibilities of thermally insulating the dividing wall is found, for example, in EP 640 367 A. A double-walled design having a narrow gas space in between is particularly favorable and therefore particularly preferred.

Preference is given to the subsection of the dividing wall column(s) (TK) divided by the dividing wall (T) consisting of subsections 2, 3, 4 and 5 or parts thereof loaded with ordered packings or random packings and the dividing wall is preferably configured with thermal insulation in these subsections.

It is further preferable that the dividing wall column(s) (TK) at the upper and lower ends of the dividing wall (T) has/have the possibility of sampling and liquid or gaseous samples are taken from the column(s) continuously or at time intervals and are investigated with respect to their composition.

Compliance with the specification for the high boilers in an intermediate boiler fraction can be regulated, for example, by the division ratio of the liquid at the upper end of the dividing wall. In this case, the division ratio of the liquid at the upper end of the dividing wall(s) (T) is adjusted such that the concentration of the key components of the high boiler fraction in the liquid at the upper end of the dividing wall accounts for, for example, 5 to 75%, typically 10 to 40%, of that which should be reached in the side takeoff product, and the liquid division is adjusted such that, in the case of higher contents of key components of the high boiler fraction more liquid and, in the case of lower contents of key components of the high boiler fraction, less liquid is partitioned to the inflow section.

Correspondingly, the specification for the low boilers in the intermediate boiler fraction can be controlled, preferably by the heat output. In this context, the heat output into the vaporizer of the respective dividing wall column is adjusted such that the concentration of key components of the low boiler fraction in the liquid at the lower end of the dividing wall(s) (T) accounts for, for example, 10 to 99%, for example about 25 to 97.5%, of the value which should be reached in the side takeoff product, and the heat output can be adjusted such that, in the case of higher content of key components of the low boiler fraction, the heat output is increased, and in the case of lower content of key components of the low boiler fraction, the heat output is reduced. Such a procedure is known in principle to those skilled in the art. Adaptation of the columns used in each case in the purification of ethoxyquin can therefore be carried out independently by a person skilled in the art on the basis of the indications provided in the present disclosure.

A further variation according to the invention of the process for the distillative workup of ethoxyquin consists in that, instead of one of the dividing wall column(s) specified—which is/are preferred in the case of a new construction with respect to the investment costs—an interconnection of two (conventional) distillation columns in the form of a thermal coupling is used (thermally coupled columns which correspond to a dividing wall column with respect to energy demand).

This is then especially favorable if the columns are already available and/or the columns are intended to be operated at different pressures.

Depending on the number of separating stages of the columns present, the most suitable forms of the interconnection can be selected.

Preference is given to two thermally coupled distillation columns each equipped with its own vaporizer and condenser.

Further preferably, the two thermally coupled columns are operated at different pressures, and only liquids can be conveyed in the connecting streams between the two columns. It is also possible to select forms of connection which only allow liquid connecting streams between the individual distillation columns to occur.

These specific interconnections offer the advantage that both distillation columns can be operated under different pressures with the advantage that heating and cooling energies available can be better adjusted to the temperature levels.

The bottom stream of the first column of the two thermally coupled columns is preferably partially or fully vaporized in an additional vaporizer and is then fed to the second column as a biphasic mixture or in the form of a gaseous and a liquid stream. In the process according to the invention, the feed stream to the column(s) is preferably partially or completely pre-vaporized and fed to the column(s) as a biphasic mixture or in the form of a gaseous and a liquid stream.

Dividing wall columns and thermally coupled columns can be designed as packed columns with random packings or ordered packings or as tray columns.

In the process according to the invention, particular preference is given to the use of a dividing wall column.

The following parameters for configuring the dividing wall column were preferably used in accordance with the invention, wherein these parameters can be selected individually in each case and the respective selections may in principle be combined with one another, wherein any dependencies are either presented in this disclosure or inherently arise:

separation stage column having a number of separating stages of preferably 10 to 100, particularly preferably 20 to 100, especially preferably 30 to 70;

operating the distillation column at 1 to 100 mbar, preferably 1 to 50, particularly preferably 1 to 20, especially preferably 1 to 10, and especially 1 to 5;

the bottom temperature of the column is set to values of 80 to 200° C., preferably of about 100 to 200, particularly preferably of 150 to 200, especially preferably of 190 to 195° C.;

the amount of bottoms liquid (volume) is from 1 to 30% of the total volume of amount of substance in the column to be separated, preferably from 1 to 20%, particularly preferably from 1 to 15, such as, for example, from 1 to 10;

the ratio of bottoms takeoff volume to amount of feed is from 0.01 to 0.3, preferably from 0.05 to 0.1;

use of packed columns, especially ordered packings; in the purifying distillation of ethoxyquin according to the invention, which is preferably operated under reduced pressure, it is recommended to use packed columns. Suitable in this case are ordered packings having a specific surface area of 100 to 1000 $m^2/m^3$, preferably about 250 to 900 $m^2/m^3$, particularly preferably about 400 to 800 $m^2/m^3$, especially preferably about 500 to 750 $m^2/m^3$. Preference is given to those packings composed of sheet metal.

the ratio of amount of reflux (FIG. 3, Number 2) to amount of feed (FIG. 3, Number 1) has a factor of from 0.5:1 to 5:1, preferably from 1:1 to 2:1 and particularly preferably from 1.3:1;

In carrying out the process according to the invention, the side takeoff comprises ethoxyquin with a purity of preferably more than 90 to 99% or more, particularly preferably more than 95 to 99% or more, such as, for example, 99.5, 99.9, 99.99, up to virtually 100 percent.

The phenetidine content in the side takeoff is preferably less than 100 ppm, preferably less than 50 ppm, particularly preferably less than 10 ppm and especially preferably less than 5 ppm such as, for example less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

The ethoxyquin according to the invention obtained by the procedure according to the invention may comprise further secondary components besides p-phenetidine. These typically originate from the synthesis of ethoxyquin and precursors thereof, and/or from decomposition processes of these substances. However, the present process can also substantially reduce these secondary components according to the purities of ethoxyquin specified above.

The process for purifying ethoxyquin is preferably carried out in accordance with the invention such that the residence time of the high boiler in the bottoms is less than 10 hours, particularly preferably less than 8 hours, especially preferably less than 5 hours, and also all values inbetween and up to 1 hour, for example 9.5, 9, 8.5, 8, 7.5, 7, 6.5, 6, 5.5, 4.5, 4, 3.5, 3, 2.5, 2, 1.5 or 1.

In the case of an increased residence time, an increased phenetidine content in the bottoms and in the side takeoff was found, such that ethoxyquin was obtained comprising significantly more than the maximum amounts in accordance with the invention of 100 ppm p-phenetidine.

Particularly preferred parameters for controlling the process according to the invention and to obtain the ethoxyquin according to the invention are the following:

1) bottoms liquid level
2) bottoms takeoff volume,
3) vacuum used,
4) number of stages used These four most important parameters can be adjusted singly, or two or more, or all at the same time with reference to the ranges according to the invention disclosed above for these parameters and their respective preferences. It is preferable to combine the respectively preferred ranges of these four parameters, particularly preferable to combine the respectively particularly preferred ranges, very particularly preferable to combine the respectively very particularly preferred ranges and especially preferable to combine the respectively especially preferred ranges.

All further parameters can also be correspondingly selected wherein preferably in each case the preferred ranges, particularly preferably the respectively particularly preferred ranges, very particularly preferably the respectively very particularly preferred ranges and especially preferably the respectively especially preferred ranges of these further parameters are combined with the four parameters specified previously as particularly preferred (bottoms liquid level, bottom takeoff volume, vacuum used, number of stages used) and their respective preferred, particularly preferred, very particularly preferred and especially preferred combinations.

Self-evidently, however, each of the parameters can be adjusted in each case, to the extent that they are independent of other parameters, such that the adjusted value for a parameter to be established falls in the general, the preferred, the particularly preferred or the especially preferred ranges, wherein the resulting dependencies of the parameters as outlined previously or the then obviously resulting free selection of the individual parameters considered in each case can be restricted. These restrictions however, optionally, inevitably arise and are therefore an inherent feature of the invention and therefore also require no further particular explanation.

Furthermore, it is possible—and in the context of this invention preferred—to heat the feed at least on start-up of the column (or the corresponding apparatus for the distillation), particularly preferably additionally during operation, and especially preferably only on start-up of the column. This heating takes place at temperatures of at least 50° C., at temperatures of up to 200° C., preferably from 80 to 190, particularly preferably from 100 to 180 and especially preferably from 120 to 170 and in particular at 140 to 160° C.

In an alternative embodiment, instead of heating the feed, the column itself can also be heated by a suitable liquid. For this purpose, this liquid, for example a heated solvent, is run into the column and therefore the column interior as well as the feeds and draws and take-offs are heated to the desired temperature, before the ethoxyquin to be purified is then run into the column (or the corresponding apparatus for distillation).

In addition to thermally insulated columns, for example by double-walled- or multi-walled-constructed column walls or parts thereof and also optionally in addition completely or partially insulated tubes of feeds and draws and take-offs, it is also conceivable to use so-called trace heating.

Trace heating means that all or at least the central parts of the column and also tubes of the feeds and draws and take-offs are heated. Heating can be effected externally (by heating jackets of any type or direct heating by open flames) or even by electrical (such as for example inductive) heating of the metal parts, for example by integrated or applied heating coils or electrical conductors or by inductive heating.

Further preferred embodiments, in addition to those described above, are the following embodiments 1 to 21 and the possibilities of combinations and back references specified in each case:

EMBODIMENT 1

A process for purifying ethoxyquin comprising p-phenetidine comprising at least one step of continuous or batchwise distillation using at least one dividing wall column or at least two thermally coupled columns, wherein ethoxyquin is obtained comprising less than 100 ppm, preferably less than 50 ppm, particularly preferably less than 10 ppm and especially preferably less than 5 ppm such as, for example, less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

EMBODIMENT 2

The process according to embodiment 1 comprising no further purification steps such as adsorption, washing, crystallization.

EMBODIMENT 3

The process according to embodiment 1 or 2, wherein the at least one column is a dividing wall column or at least one of the at least two coupled columns is a dividing wall column.

EMBODIMENT 4

The process according to embodiment 3, wherein the dividing wall column has a dividing wall (T) in the longitudinal direction of the column forming an upper (C) and lower (D) common column region, an inflow section (A) and an offtake section (B), and the mixture to be separated is fed to the middle part of the inflow region and the product ethoxyquin is removed from the middle region of the offtake section.

EMBODIMENT 5

The process according to embodiment 3 or 4, wherein the dividing wall of the dividing wall column is extended in a continuous manner either up to the upper or down to the lower end of the distillation column or up to the upper and down to the lower end.

EMBODIMENT 6

The process according to any of preceding embodiments, wherein only one column, and said column in the form of a dividing wall column, is used.

EMBODIMENT 7

The process according to any of the preceding embodiments, wherein the dividing wall column (TK) has a dividing wall (T) in the longitudinal direction of the column forming an upper common column region (1), a lower common column region (6), an inflow section (2, 4) with rectifying section (2) and stripping section (4), and an offtake section (3, 5) with rectifying section (5) and stripping section (3), wherein the mixture to be separated (feed) is fed to the middle region of the inflow section (2, 4), the high boiler fraction is removed via the bottom (bottom takeoff C), the low boiler fraction is removed via the overhead (top takeoff A) and the intermediate boiler fraction is removed from the middle region of the offtake section (3, 5) (side takeoff B).

EMBODIMENT 8

The process according to any of the preceding embodiments, wherein the dividing wall column(s) have 30 to 100, in particular 50 to 90 theoretical plates.

EMBODIMENT 9

The process according to any of the previous embodiments, wherein the upper common column region (1) of the dividing wall column(s) (TK) has 5 to 50%, preferably 20 to 35%, the rectifying section (2) of the inflow section (2, 4) of the column has 5 to 50%, preferably 10 to 20%, the stripping section (4) of the inflow section of the column has 5 to 50%, preferably 20 to 35%, the rectifying section (3) of the offtake section (3, 5) of the column has 5 to 50%, preferably 7 to 20%, the stripping section (5) of the offtake section of the column has 5 to 50%, preferably 20 to 35%, and the common lower region (6) of the column has 5 to 50%, preferably 20 to 35%, of the total number of theoretical plates (nth) of the column.

EMBODIMENT 10

The process according to any of the preceding embodiments, wherein in the dividing wall column(s) (TK), in each case the sum of the number of theoretical plates of the subregions (2) and (4) in the inflow section is 80 to 110%, preferably 90 to 100%, of the total of the number of plates of the subsections (3) and (5) in the offtake section.

EMBODIMENT 11

The process according to any of the preceding embodiments, wherein the dividing wall section has 40-80%, preferably 50-70%, the upper common column section has 5-50%, preferably about 15-20%, the lower common column section has 5-50%, preferably about 15-20%, of the theoretical plates of the dividing wall column.

EMBODIMENT 12

The process according to any of the preceding embodiments, wherein the column(s) has/have at least one heat exchanger as vaporizer and at least one heat exchanger as condenser for each column used.

EMBODIMENT 13

The process according to any of the preceding embodiments, wherein the at least one column is configured in each case as double-walled or multi-walled, preferably double-walled, having at least one gas space between the at least two walls.

EMBODIMENT 14

The process according to any of the preceding embodiments, wherein the upper common column region (1) of the dividing wall column(s) (TK) has 5 to 50%, preferably 20 to 35%, the rectifying section (2) of the inflow section (2, 4) of the column has 5 to 50%, preferably 10 to 20%, the stripping section (4) of the inflow section of the column has 5 to 50%, preferably 20 to 35%, the rectifying section (3) of the offtake section (3, 5) of the column has 5 to 50%, preferably 7 to 20%, the stripping section (5) of the offtake section of the column has 5 to 50%, preferably 20 to 35%, and the common lower region (6) of the column has 5 to 50%, preferably 20 to 35%, of the total number of theoretical plates (nth) of the column, and wherein the subsection of the dividing wall column(s) (TK) divided by the dividing wall (T) consisting of subsections 2, 3, 4 and 5 or parts thereof is loaded with ordered packings or random packings, and the column(s) is filled at least partially with random packings or ordered packings, preferably ordered packings, particularly preferably those composed of sheet metal.

EMBODIMENT 15

The process according to any of the preceding embodiments, wherein
A) the separation stage column has a number of separating stages of preferably 10 to 100, particularly preferably 20 to 100, especially preferably 30 to 70;
B) the distillation column is operated at 1 to 100 mbar, preferably 1 to 50, particularly preferably 1 to 20, especially preferably 1 to 10, and especially 1 to 5;
C) the bottom temperature of the column is set to values of 80 to 200° C., preferably of about 100 to 200, particularly preferably of 150 to 200, especially preferably of 190 to 195° C.;
D) the amount of bottoms liquid (the volume) is from 1 to 30% of the total volume of amount of substance in the column to be separated, preferably from 1 to 20%, particularly preferably from 1 to 15, such as, for example, from 1 to 10;
E) the ratio of bottoms takeoff volume to amount of feed is from 0.01 to 0.3, preferably from 0.05 to 0.1;
F) packed columns, particularly ordered packings, and especially sheet metal packings are used having a specific surface area of 100 to 1000 $m^2/m^3$, preferably about 250 to 900 $m^2/m^3$, particularly preferably about 400 to 800 $m^2/m^3$, especially preferably about 500 to 750 $m^2/m^3$; and
G) the ratio of amount of reflux to amount of feed has a factor from 0.5:1 to 5:1, preferably from 1:1 to 2:1 and particularly preferably 1.3:1.

EMBODIMENT 16

The process according to embodiment 15, wherein the residence time of the high boiler in the bottoms is less than 10 hours, particularly preferably less than 8 hours, especially preferably less than 5 hours, and also all values inbetween and up to 1 hour, for example 9.5, 9, 8.5, 8, 7.5, 7, 6.5, 6, 5.5, 4.5, 4, 3.5, 3, 2.5, 2, 1.5 or 1.

EMBODIMENT 17

The process according to any of the preceding embodiments, wherein the column(s) are traceheated.

EMBODIMENT 18

The process according to any of the preceding embodiments, wherein at least at the start-up the feed is pre-heated to a temperature of at least 50° C. up to 200° C., preferably from 80 to 190, particularly preferably from 100 to 180 and especially preferably from 120 to 170 and in particular at 140 to 160° C.

EMBODIMENT 19

Ethoxyquin obtainable by a process according to any of embodiments 1 to 18 comprising less than 100 ppm, preferably less than 50 ppm, particularly preferably less than 10 ppm and especially preferably less than 5 ppm such as, for example, less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

EMBODIMENT 20

Ethoxyquin comprising less than 100 ppm, preferably less than 50 ppm, particularly preferably less than 10 ppm and especially preferably less than 5 ppm such as, for example less than 1 ppm or even less than 0.5 ppm p-phenetidine and also all values inbetween, for example less than 90, 80, 70, 60, 45, 40, 35, 30, 25, 20, 15, 9, 8, 7, 6, 4, 3, 2, 0.9, 0.8, 0.7, 0.6, 0.4, 0.3, 0.2 or less than 0.1.

EMBODIMENT 21

The use of ethoxyquin according to embodiment 19 or 20 as additive in foodstuffs and feedstuffs, preferably in feedstuffs, particularly preferably as antioxidant in feedstuffs and feed additives.

Laboratory analysis of p-phentidine and EQ is by gas chromatography. The corresponding residence times and methodology are known to those skilled in the art and can optionally also be very simply determined and validated. The principal procedure for this purpose including the validation is known to those skilled in the art. Any methods of gas chromatography are therefore suitable if they afford an appropriate precision for p-phenetidine in ethoxyquin, which can be readily determined by validation using calibrated samples comprising ethoxyquin and standardized amounts of p-phenetidine.

EXAMPLES

Experiments according to the invention—Table 1 Variation of distillation parameters of laboratory distillation on dividing wall column; ethoxyquin ("crude" distillate; comprises 0.18 g (=1800 ppm) p-phenetidine

TABLE 1

| Experiment | Feed g/h | Return stream g/h | Pressure (top) [mbar] | Temp. bottoms ° C. | Temp. overhead C. | Temp. Main condenser C. | Overhead takeoff g/h | Bottom takeoff g/h | Side takeoff g/h | Phenetidine in the product of the side takeoff [ppm] |
|---|---|---|---|---|---|---|---|---|---|---|
| 1 | 302 | 466 | 12 | 168 | 160 | 60 | 65 | 104 | 215 | 5 |
| 2 | 301 | 442 | 12 | 171 | 159 | 60 | 30 | 22 | 236 | 5 |
| 3 | 284 | 403 | 12 | 172 | 158 | 60 | 25 | 22 | 234 | 5 |
| 4 | 274 | 400 | 17 | 179 | 164 | 60 | 25 | 20 | 228 | 6 |
| 5 | 284 | 400 | 22 | 188 | 169 | 60 | 26 | 31 | 225 | 5 |
| 6 | 285 | 399 | 30 | 196 | 175 | 90 | 26 | 30 | 226 | 8 |
| 7 | 284 | 421 | 35 | 201 | 179 | 90 | 30 | 26 | 226 | 8 |
| 8 | 247 | 406 | 35 | 200 | 179 | 90 | 28 | 37 | 182 | 6 |
| 10* | 250 | 399 | 35 | 198 | 178 | 90 | 26 | 40 | 183 | 3 |

*experiment 10 with upstream thin film evaporator

It can be derived from experiments 1 to 10 that it is desirable to establish a low thermal load (i.e. low temperature) in the distillation, in order to avoid decomposition reactions of high boilers, mostly in the bottoms. Furthermore, it is preferable to maintain a low residence time of the components in the bottoms.

Non-Inventive Example

Depletion of p-phenetidine from ethoxyquin by acidic extraction.

Principal procedure: the organic phase comprising "crude" distilled ethoxyquin (comprises 0.18 g—corresponding to 1800 ppm p-phenetidine) was washed repeatedly with aqueous acidic solution. Phase separation then took place. The phases were sampled for ethoxyquin and p-phenetidine contents.

Specific procedure of the experiments conducted:

500 mL of ethoxyquin, 250 mL of water, 23 g of aqueous phosphoric acid (content 85%) were stirred overnight. Addition of 23 g of aqueous phosphoric acid (content 85%).

The resulting phases were separated (upper organic phase, lower aqueous phase)

lower phase: set to pH12 with about 200 ml of aqueous sodium hydroxide solution (content 25%).

upper phase (organic): Addition of 250 ml of water and 23 g of aqueous phosphoric acid (content 85%); stir overnight. phase separation; lower phase (aqueous) again separated off; addition to the fresh lower phase of about 200 mL of aqueous sodium hydroxide solution (content 25%) to pH 12.

After extraction, both the ethoxyquin used for the acidic extraction and the extract were investigated for the ethoxyquin and phenetidine contents. No significant depletion or enrichment was found, that is to say the value for p-phenetidine was in the same range as prior to treatment.

Explanation of FIG. 2: (A)=top takeoff; (B)=side takeoff; (C)=bottom takeoff; (F)=feed; (T)=dividing wall; (WZ)=heat supply; (WA)=heat removal; (TK)=dividing wall column; upper common column region (1); lower common column region (6); inflow section (2, 4) with rectifying section (2) and stripping section (4); offtake section (3, 5) with rectifying section (5) and stripping section (3); feed of the mixture (feed) (F) to be separated to the middle region of the inflow section (2, 4);

Dividing wall column schematic (FIG. 3); explanation:

Feed 1); reflux (portion of the vapor stream) 2); top takeoff 3); bottom takeoff with partial recirculation 4) into the lower common section of the column; side takeoff 5); inflow section (A); offtake section (B); upper common section of the column (C); lower common section of the column (D); dividing wall (T).

The invention claimed is:

1. A process for purifying ethoxyquin comprising p-phenetidine, comprising at least one step of continuous distillation using at least one dividing wall column, wherein ethoxyquin is obtained comprising less than 100 ppm p-phenetidine, wherein
   A) the at least one dividing wall column has a number of separation stages of 10 to 100;
   B) the at least one dividing wall column is operated at 1 to 100 mbar;
   C) the bottom temperature of the at least one dividing wall column is set to values of 80 to 200° C.;
   D) the amount of bottoms liquid (the volume) is from 1 to 30% of the total volume of the amount of substance to be separated in the at least one dividing wall column;
   E) a ratio of bottoms takeoff volume to the amount of feed is from 0.01 to 0.3;
   F) packed columns with structured packings of a specific surface area of 100 to 1000 $m^2/m^3$ are used; and
   G) a ratio of amount of reflux to amount of feed has a factor of from 0.5:1 to 5:1.

2. The process according to claim 1, wherein the at least one dividing wall column has a dividing wall (T) in the longitudinal direction of the column forming an upper (1) and lower (6) common column region, an inflow section (A) and an offtake section (B), and the mixture to be separated is fed to the inflow region and the product ethoxyquin is removed from a side offtake;
   wherein the upper common column region is situated above the dividing wall(T) and contains 5 to 50% and the lower common column region is situated below the dividing wall (T) and contains 5 to 50% of the total number of theoretical plates in the column.

3. The process according to claim 2, wherein the dividing wall column (TK) has a dividing wall (T) in the longitudinal direction of the column forming an upper common column region, a lower common column region, an inflow section with rectifying section and stripping section, and an offtake section with rectifying section and stripping section, wherein the mixture to be separated (feed) is fed to the inflow section, a first fraction is removed via the bottom (bottom takeoff C), a second fraction is removed via the overhead (top takeoff A) and a third fraction is removed from the offtake section (side takeoff B).

4. The process according to claim 3, wherein the upper common column region of the at least one dividing wall column (TK) has 5 to 50%, the rectifying section of the inflow section of the column has 5 to 50%, the stripping section of the inflow section of the column has 5 to 50%, the rectifying section of the offtake section of the column has 5 to 50%, the stripping section of the offtake section of the column has 5 to 50%, and the lower common lower region of the column has 5 to 50%, of the total number of theoretical plates (nth) of the column.

5. The process according to claim 3, wherein in the at least one dividing wall column (TK), in each case the sum of the number of theoretical plates of the inflow section is 80 to 110% of the total of the number of plates of the subsections (3) and (5) in the offtake section.

6. The process according to claim 2, wherein the upper common column region (1) of the at least one dividing wall column (TK) has 5 to 50%, the rectifying section (2) of the inflow section (2, 4) of the column has 5 to 50%, the stripping section (4) of the inflow section of the column has 5 to 50%, the rectifying section (3) of the offtake section (3, 5) of the column has 5 to 50%, the stripping section (5) of the offtake section of the column has 5 to 50%, and the lower common column region (6) of the column has region (6) of the column has 5 to 50%, of the total number of theoretical plates (nth) of the column, and wherein the subsection of the dividing wall column(s) (TK) divided by the dividing wall (T) consisting of subsections 2, 3, 4 and 5 or parts thereof is loaded with ordered packings or random packings, and the column(s) is filled at least partially with random packings or ordered packings.

7. The process according to claim 1, wherein only one column, and said column in the form of a dividing wall column, is used.

8. The process according to claim 1, wherein the at least one dividing wall column has 30 to 100 theoretical plates.

9. The process according to claim 1, wherein the dividing wall section has 40 to 80%, the upper common column region has 5 to 50%, the lower common column region has 5 to 50%, of the total number of theoretical plates of the dividing wall column.

10. The process according to claim 1, wherein a fraction is removed from via the bottom, wherein the residence time of the fraction in the bottoms is less than 10 hours.

11. A process for producing an ethoyquin-containing foodstuff or feedstuff, wherein in step
1) a crude ethoxyquin product is subjected to at least one step of continuous distillation using at least one dividing wall column or at least two thermally coupled columns, wherein at least one of the at least two coupled columns is a dividing wall column, wherein
   A) the at least one column has a number of separation stages of 10 to 100;
   B) the at least one column is operated at 1 to 100 mbar;
   C) the bottom temperature of the at least one column is set to values of 80 to 200° C.;
   D) the amount of bottoms liquid (the volume) is from 1 to 30% of the total volume of the amount of substance to be separated in the at least one column;
   E) the ratio of bottoms takeoff volume to the amount of feed is from 0.01 to 0.3;
   F) packed columns with ordered packings of a specific surface area of 100 to 1000 $m^2/m^3$ are used; and
   G) the ratio of amount of reflux to amount of feed has a factor of from 0.5:1 to 5:1, and
   H) a fraction is removed from via the bottom, wherein the residence time of the fraction in the bottoms is less than 5 hours;
   wherein the process according to step 1 does not comprise any subsequent ethoxyquin purification steps;
2) from the process of step 1, ethoxyquin having a p-phenetidine content of less than 50 ppm is obtained, and
3) the ethoxyquin obtained in step 2 is incorporated in a foodstuff or feedstuff.

* * * * *